United States Patent [19]

Leung et al.

[11] Patent Number: 6,090,381
[45] Date of Patent: Jul. 18, 2000

[54] STIMULATION OF AN IMMUNE RESPONSE WITH ANTIBODIES LABELED WITH THE α-GALACTOSYL EPITOPE

[75] Inventors: Shui-on Leung, Madison; Zhengxing Qu, Warren, both of N.J.

[73] Assignee: Immunomedics, Inc., Morris Plains, N.J.

[21] Appl. No.: 09/020,299

[22] Filed: Feb. 6, 1998

Related U.S. Application Data

[60] Provisional application No. 60/037,908, Feb. 11, 1997.
[51] Int. Cl.[7] .................................................. A61K 39/395
[52] U.S. Cl. .................................... 424/130.1; 424/133.1; 424/137.1; 424/138.1; 424/141.1; 424/142.1; 424/155.1; 424/174.1
[58] Field of Search ............................ 424/130.1, 133.1, 424/137.1, 138.1, 141.1, 142.1, 147.1, 150.1, 151.1, 155.1, 174.1

[56] References Cited

FOREIGN PATENT DOCUMENTS

WO 95/24924  9/1995  WIPO .
97/23637  7/1997  WIPO .

OTHER PUBLICATIONS

Borrebaeck et al., "Immunology Today", Does endogenous glycosylation prevent the use of mouse monoclonal antibodies as cancer therapeutics?, vol. 14, No. 10, pp. 477–479, (1993).
Thall et al., "Biochemistry", *Distribution of Galα1→3Galβ1→4GlcNAc Residues on Secreted Mammalian Glycoproteins (Thyroglobulin, Fibrinogen, and Immunoglobulin G) As Measured by a Sensative Solid–Phased Radioimmunoassay*, 29, pp. 3959–2965, (1990).
LaTemple et al., "Cancer Research", Synthesis of α–Galactosyl Epitopes by Recombinant α1,3Galactosyltransferase for Opsonization of Human Tumor Cell Vaccines by Anti–Galactose, vol. 56, pp. 3069–3074, (Jul., 1996).
Leung et al., "The Journal of Immunology", Engineering a Unique Glycosylation Site for Site–Specific Conjugation of Haptens to Antibody Fragments[1], vol. 154, pp. 5919–5926, (1995).
Leung et al., "Int. J. Cancer", Effect of VK Framework–1 Glycosylation on the Binding Affinity of Lymphoma–Specifc Murine and Chimeric LL2 Antibodies and its Potential Use as a Novel Conjugation Site, 60, pp. 534–538, (1995).
Galili, "Immunology Today", Interaction of the natural anti–Gal antibody with α–galactoslyl epitopes: a major obstacle for xenotransplantation in humans, vol. 14, No. 10, pp. 480–482, (1993).
Qu et al., "Glycobiology", Structure determination of N–linked oligosaccharides engineered at the $CH_1$ domain of humanized LL2, vol. 7, No. 6, pp. 803–809, (1997).
U. Galili et al., "A Unique Natural Human IgG Antibody with Anti–α–Galactosyl Specificity" J. Exp Med. vol. 160, Nov. 1984, pp. 1519–1531.
J.L. Avila et al., "Immunogenic Galα1→3Gal Carbohydrate Epitopes are Present on Pathogenic American Trypanosoma and Leishmania", J. of Immun., vol. 142, No. 8, (1989) pp. 2828–2834.
U. Galili et al., "α–Galactosyl (Galα;=3Galβ1–4GlcNac–R) epitopes on human cells: synthesis of the epitope on human red cells by recombinant primate", Glycobiology, vol. 5, No. 8, pp. 775–782, (1995).
U. Galili et al., "Human Natural Anti–α–Galactosyl lgG", J. Exp. Med., vol. 162, (Aug. 1985), pp. 573–582.
U. Galili et al., "Evolutionary relationship between the natural anti–Gal antibody and the Galα1→epitope in primates" Proc. Natl. Acad. Sci., vol. 84, pp. 1369–1373, (1987).
U. Galili et al., "Man, Apes, and Old World Monkeys Differ from Other Mammals in the Expression of α–Galactosyl Epitopes on Nucleated Cells", J. Biol. Chem., vol. 263, pp. 17755–17762, (1988).
U. Galili et al., "A Unique Natural Human IgG Antibody with Anti–αGalactosyl Spacificity", J. Exp. Med. vol. 160, pp. 1519–1531, (1984).
F.A. Neethling et al., Protection of Pig Kidney (PK15) Cells from the Cytotoxic Effect of Anti–Pig Antibodies by α–Galactosyl Olig., Transplantation, vol. 57, pp. 959–963, (1994).
U. Galili et al., "Inhibition of Anti–Gal IgG Binding to a Porcine Endothelial Cells by Synthetic Oligosaccharides", Transplantation, bol. 62, No. 2, pp. 256–262, (1996).
R.P. Rother et al., "A Novel Mechanism of Retrovirus Inactivation in Human Serum Mediated by Anti–α–Galactosyl Natural Antibody", J. Exp. Med., vol. 182, pp. 1345–1355, (1995).
Milenic, D. et al, Int. J. Biol. Markers, (1990) 5(4), 177–187.
Patel, T. et al., Biochem. J. (1992) 285, 839–845.
Coding, J. Monoclonal Antibodies:Princ. & Practice (1983) pp. 119–123.

*Primary Examiner*—Nancy A. Johnson
*Assistant Examiner*—Alana M. Harris
*Attorney, Agent, or Firm*—Foley & Lardner

[57] ABSTRACT

Humoral and cellular immune responses against tumor cells and infectious agents are induced in a mammal using an antibody that binds with an epitope of an antigen that is associated with a tumor or an infectious agent, and that contains at least one α-galactosyl epitope. Such an antibody is capable of forming a complex with cells that express the target epitope and with antibodies that bind α-galactosyl epitopes. Suitable antibodies include molecules that contain at least one engineered glycosylation site in the constant region of the heavy chain.

6 Claims, 6 Drawing Sheets

(1 of 6 Drawing Sheet(s) Filed in Color)

FIG. 1

HUMAN IgG1 CH1 DOMAIN (FROM AMINO ACIDS 149-207):

```
            149                  162                                                    198        207
            *                    *                                                      *          *
CH1    PEPVT   VSWNSGAL   TSG   VHTFPAVLQS   SG   LYSLSSVVTV   PSSSLGTQT   YI
HCN1   PEPVT   VSWNSSAL   TSG   VHTFPAVLQS   SG   LYSLSSVVTV   PSSSLGTQT   YI
HCN5   PEPVT   VSWNSGAL   TSG   VHTFPAVLQS   SG   LYSLSSVVTV   PSSSNGTQT   YI

β-STRAND:         C                   D                  E
```

FIG.4

THE STRUCTURES OF CH₁-APPENDED OLIGOSACCHARIDES

| HCN1-CHO | STRUCTURE ASSIGNMENT | HCN5-CHO | STRUCTURE ASSIGNMENT |
|---|---|---|---|
|  |  | N5-a |  |
| N1-b |  | N5-b1 |  |
|  |  | N5-b2 |  |
| N1-c |  | N5-c |  |

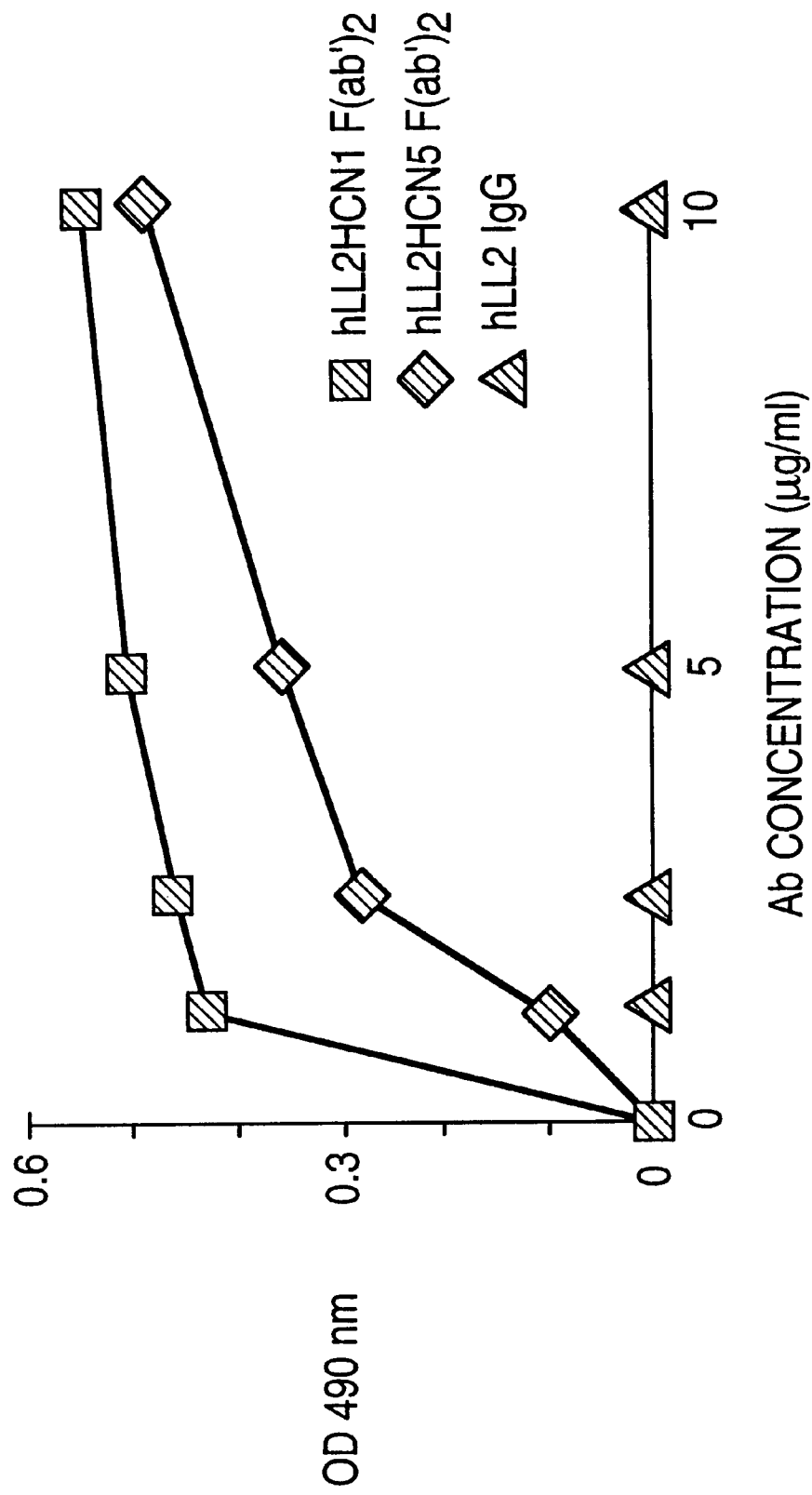

STIMULATION OF AN IMMUNE RESPONSE WITH ANTIBODIES LABELED WITH THE α-GALACTOSYL EPITOPE

This application claims priority to provisional application 60/037,908, filed Feb. 11, 1997, now abandoned.

BACKGROUND OF THE INVENTION

1. Field of the Invention

The present invention relates to methods for inducing humoral and cellular immune responses against tumor cells and infectious agents. In particular, this invention is directed to methods for stimulating an immune response using an antibody that binds with an epitope of an antigen that is associated with a tumor or an infectious agent, and that contains at least one α-galactosyl epitope. The present invention also is directed to mutated antibodies that contain at least one α-galactosyl epitope in an engineered glycosylation site located in the constant region of the heavy chain.

2. Related Art

Transplants performed between phylogenetically disparate species are known to be susceptible to hyperacute rejection which is initiated by binding of xenoreactive natural antibodies to endothelium in the donor organ. Binding of these antibodies activates complement, leading to tissue injury and destruction of the graft. For example, porcine organs transplanted into primates are nearly always rejected within hours. Fukushima et al., *Transplantation* 57:923 (1994); Pruitt et al., *Transplantation* 57:363 (1994).

The major xenoantigen responsible for such rejection has recently been identified as a single carbohydrate structure, the α-galactosyl epitope (Galα1-3Galβ1-4GlcNAc-R). Galili et al., *J. Exp. Med.* 162:573 (1985); Galili et al., *Proc. Nat'l Acad. Sci. USA* 84:2369 (1987); Galili et al., *J. Biol. Chem.* 263:17755 (1988). The α-galactosyl epitope is a glycosidic moiety that is expressed on the surface of cells from most mammalian species excluding humans and other old World primates (catarrhine primates). Expression of the α-galactosyl epitope is mediated by the α1, 3galactosyl transferase, an enzyme which is absent in old World primates and humans. In humans, as much as 1% of the total serum IgG is specific for the α-galactosyl epitope. Galili et al., *J. Exp. Med.* 160:1519 (1984); Avila et al., *J. Immunol.* 142:2828 (1989). Significant levels of anti-α-galactosyl ("anti-Gal") IgM and IgA have also been reported.

Recently, LaTemple et al., *Cancer Res.* 56:3069 (1996), reported their studies on conferring xenograft characteristics to human cells by ex vivo treatment of tumor cells with neuraminidase and recombinant α1,3galactosyl transferase. The reaction converts the sialylated N-acetyllactosamine found on the human cell surface carbohydrate moieties into the α-galactosyl epitope. Tumor cells armed with this epitope were reintroduced to the patients. The results indicated that anti-Gal antibodies help opsonize the tumor cells for phagocytosis by professional antigen presenting cells. LaTemple et al. hypothesized that the antigen presenting cells, after ingesting the "armed" tumor cells (tumor vaccines), would present the appropriate tumor-associated antigens (TAAs) to T cells, and that the patient would eventually develop a tumor-specific immunity. The exploitation of the hyperacute rejection mediated by anti-Gal activated complement, however, will require all tumor cells to be "induced" with the α-galactosyl epitope, and was not and could not be addressed by this approach. Moreover, the vaccines of LaTemple et al. require removal of a patient's tumor cells, in vitro treatment with enzymes to produce the α-galactosyl epitope, washing and lethal irradiation.

Galili et al., international publication No. WO 95/24924, describe a more general method for enhancing the immune response to an antigen by positioning an α-galactosyl epitope either on or juxtaposed to the target antigen. According to this method, such a mixture stimulates opsonization by binding anti-Gal to α-galactosyl epitopes which increases phagocytosis and subsequent processing of the target antigen by the macrophages. This general approach, however, also requires numerous ex vivo steps.

Therefore, the α-galactosyl epitope has potential as a means to enhance the immune response to a target antigen, but a need exists for a method that does not depend upon extensive in vitro manipulation.

SUMMARY OF THE INVENTION

Accordingly, it is an object of the present invention to provide a method for enhancing the immune response to a tumor cell or infectious agent by using antibodies that contain the α-galactosyl epitope to induce a patient's immune system to target an antigen associated with the tumor cell or infectious agent.

Another object of this invention is to provide mutated antibodies that contain at least one engineered glycosylation site with a carbohydrate moiety comprising at least one α-galactosyl epitope.

These and other objects are achieved, in accordance with one embodiment of the present invention by the provision of a method for stimulating humoral and cellular immune responses in a mammal against a tumor that expresses a tumor associated antigen (TAA) or against a disease caused by an infectious agent, comprising the step of:

(a) administering an α-Gal antibody to the mammal, wherein the α-Gal antibody comprises:
 (i) an antibody component that binds with a specified target epitope, wherein the target epitope is an epitope of a TAA or an epitope of an antigen associated with an infectious agent, and
 (ii) at least one α-galactosyl epitope,
 wherein the α-Gal antibody can form a complex with cells that express said target epitope and antibodies that bind the α-galactosyl epitope.

BRIEF DESCRIPTION OF THE DRAWINGS

The file of this patent contains at least drawing executed in color. Copies of this patent with color drawing will be provided by the Patent and Trademark Office upon request and payment of the necessary fee.

FIG. 1 provides a comparison of the engineered glycosylation sites in hLL2HCN1 (SEQ ID No:2) and hLL2HCN5 (SEQ ID No:3) in the human IgG1 CH1 domain (SEQ ID No:1).

FIG. 4 summarizes structures of CH1-appended oligosaccharides in hLL2HCN1 and hLL2HCN5. The figure identifies locations of fucose (open triangle), sialic acid (grey triangle), N-acetylglucosamine (square), mannose (open circle), β-galactose (grey circle), and α-galactose (black circle). Sialic acid residues having undetermined linkage sites are shown without a link. α-Galactosyl epitopes are enclosed by boxes.

FIG. 6 shows the results of an enzyme-linked immunosorbent assay used to detect the presence of the α-galactosyl epitope in whole humanized LL2 antibody and in hLL2 fragments that contain engineered glycosylation sites.

DETAILED DESCRIPTION

1. Overview

Figure 2:
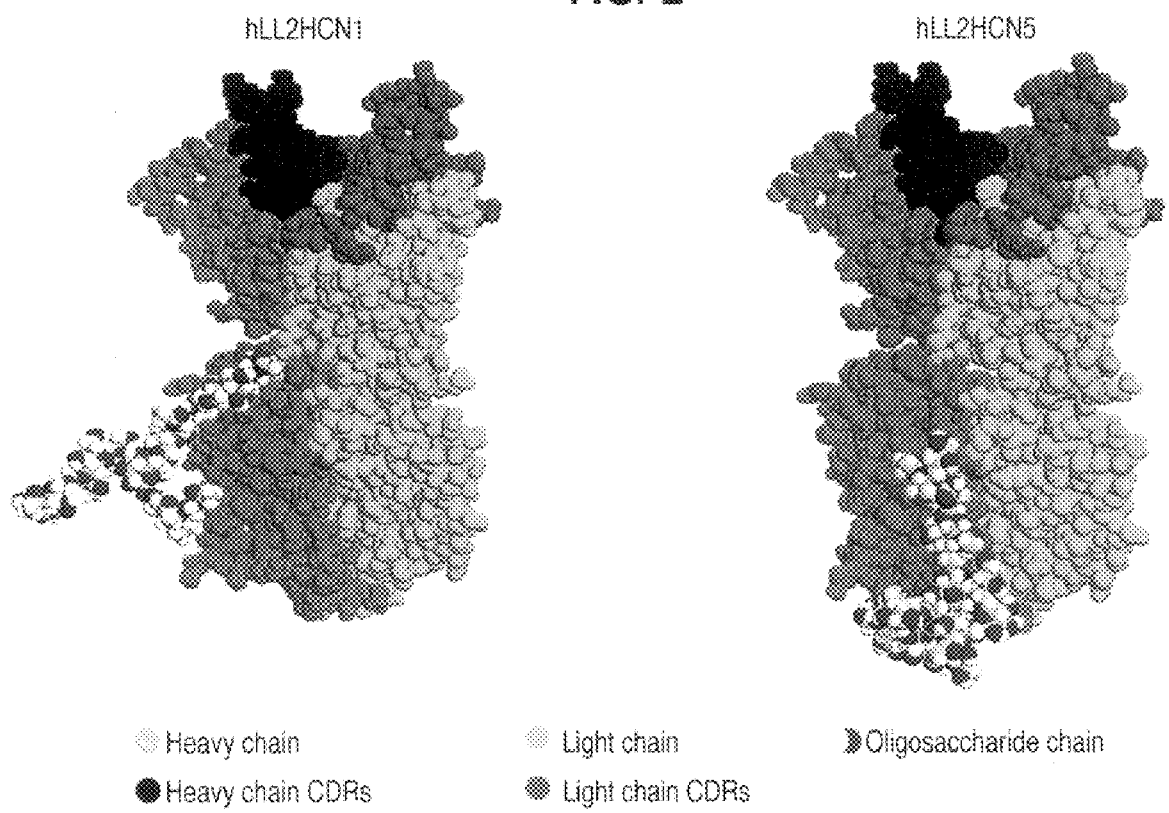
FIG. 2 shows a computer model illustrating the locations of carbohydrates bound to engineered glycosylation sites in Fab fragments of hLL2HCN1 and hLL2HCN5.

Most monoclonal antibodies (MAbs) used for the treatment of cancers and other diseases are either conjugated to radionuclides, drugs, toxins, or other cytotoxic agents. These effector molecules, however, have caused a variety of problems, such as organ toxicity and immunogenicity, that would limit or negate the therapeutic effect of the immunoconjugates.

Raff et al., Blood 83:435 (1994), reported the in vivo depletion of B cells by a chimeric mouse human MAb to CD20, C2B8, and they proposed to use unlabeled C2B8 for the treatment of B-cell lymphoma. Phase I clinical trials using escalating single-dose infusion of C2B8 in patients with recurrent B-cell lymphoma has produced tumor regression in six of fifteen cases. Maloney et al., Blood 84:2457 (1994). Data suggest that tumor-specific cell killing occurred via complement (CDCC)- and antibody (ADCC)-dependent cell-mediated lysis. However, only a few antibodies specific for certain defined antigens will have such desirable characteristics, and these properties are not transferable to other antibodies with different antigen specificities.

As discussed above, LaTemple et al. and Galili et al. proposed methods for using the α-galactosyl epitope to enhance the immune response to a target antigen. Their approach of combining the target antigen with the α-galactosyl epitope in vitro, however, requires extensive ex vivo manipulation. In contrast, the present invention provides a means to take advantage of the α-galactosyl epitope in the context of Mab treatment that overcomes the deficiencies of the LaTemple/Galili method and established Mab immunotherapy. Specifically, the present invention provides Mabs containing at least one α-galactosyl epitope that are used to (1) elicit a hyperacute type of xenorejection response against tumors or infectious agents bound with the therapeutic antibody carrying the α-galactosyl epitope, and (2) to opsonize tumor cells or infectious agents coated with the α-galactosyl-antibody for the generation of immunity against the tumor cells or infectious agent targets.

According to the methods of the present invention, when targets are bound with an α-galactosyl-antibody, the targets will appear as a xenograft to the human host, and a hyperacute xenograft rejection response will be mounted against the target cells via complement activation. Moreover, the circulating endogenous anti-α-galactosyl antibodies will serve to opsonize the target cells and facilitate their phagocytosis by professional antigen presenting cells, thereby allowing the antigen presenting cells to sort out the proper target-specific antigen for presentation, and to develop a humoral and cellular immunity against the target cells. This approach also can be used to increase the immunogenicity of proteins or other molecules that are characteristically poor in eliciting an immune response.

2. Definitions

In the description that follows, a number of terms are utilized extensively. Definitions are herein provided to facilitate understanding of the invention.

Anti-Gal. "Anti-Gal" refers to antibodies that bind with the α-galactosyl epitope (Galα1-3Galβ1-4GlcNAc-R).

α-Gal Antibody. As used herein, an α-Gal antibody is an antibody that contains one or more α-galactosyl epitopes.

Mutated Antibody.

As used herein, a mutated antibody comprises a constant region that contains at least one engineered glycosylation site.

Chimeric mLL2 Antibody.

A chimeric mLL2 antibody is a recombinant antibody that contains the kappa light-chain variable region of the murine LL2 antibody. Although the term "chimeric mLL2 antibody" includes antibody fragments and whole antibodies, the term does not include whole mLL2 antibody per se.

Structural gene.

A DNA sequence that is transcribed into messenger RNA (mRNA) which is then translated into a sequence of amino acids characteristic of a specific polypeptide.

Promoter.

A DNA sequence which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent if the promoter is a constitutive promoter.

Enhancer.

A promoter element. An enhancer can increase the efficiency with which a particular gene is transcribed into mRNA irrespective of the distance or orientation of the enhancer relative to the start site of transcription.

Complementary DNA (cDNA).

Complementary DNA is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complement.

Expression.

Expression is the process by which a polypeptide is produced from a structural gene. The process involves transcription of the gene into mRNA and the translation of such mRNA into polypeptide(s).

Cloning vector.

A DNA molecule, such as a plasmid, cosmid, phagemid, or bacteriophage, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene which is suitable for use in the identification and selection of cells transformed with the cloning vector. Marker genes typically include genes that provide tetracycline resistance or ampicillin resistance.

Expression vector.

A DNA molecule comprising a cloned structural gene encoding a foreign protein which provides the expression of the foreign protein in a recombinant host. Typically, the expression of the cloned gene is placed under the control of (i.e., operably linked to) certain regulatory sequences such as promoter and enhancer sequences. Promoter sequences may be either constitutive or inducible.

Recombinant Host.

A recombinant host may be any prokaryotic or eukaryotic cell which contains either a cloning vector or expression vector. This term is also meant to include those prokaryotic or eukaryotic cells that have been genetically engineered to contain the cloned gene(s) in the chromosome or genome of the host cell. For examples of suitable hosts, see Sambrook et al., MOLECULAR CLONING: A LABORATORY MANUAL, Second Edition, Cold Spring Harbor Laboratory, Cold Spring Harbor, N.Y. (1989).

A tumor associated antigen is a protein normally not expressed, or expressed at very low levels, by a normal counterpart. Examples of tumor associated antigens include α-fetoprotein and carcinoembryonic antigen (CEA). Many other illustrations of tumor associated antigens are known to those of skill in the art. See, for example, Urban et al., *Ann. Rev. Immunol.* 10:617 (1992).

As used herein, an infectious agent denotes both microbes and parasites. A "microbe" includes viruses, bacteria, rickettsia, mycoplasma, protozoa, fungi and like microorganisms. A "parasite" denotes infectious, generally microscopic or very small multicellular invertebrates, or ova or juvenile forms thereof, which are susceptible to antibody-induced clearance or lytic or phagocytic destruction, such as malarial parasites, spirochetes, and the like.

Humanized antibodies are recombinant proteins in which murine complementary determining regions of monoclonal antibodies have been transferred from heavy and light variable chains of the murine immunoglobulin into a human variable domain.

As used herein, the term antibody component includes both an entire antibody and an antibody fragment.

3. Methods for Preparing an α-Gal Antibody

A. Production of Rodent Monoclonal Antibodies, Humanized Antibodies, Primate Antibodies and Human Antibodies An α-Gal antibody of the present invention may be derived from a rodent monoclonal antibody. Rodent monoclonal antibodies to specific antigens may be obtained by methods known to those skilled in the art. See, for example, Kohler and Milstein, *Nature* 256:495 (1975), and Coligan et al. (eds.), CURRENT PROTOCOLS IN IMMUNOLOGY, VOL. 1, pages 2.5.1–2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

Mabs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in METHODS IN MOLECULAR BIOLOGY, VOL. 10, pages 79–104 (The Humana Press, Inc. 1992).

A wide variety of monoclonal antibodies against tumor associated antigens or infectious agents have been developed. See, for example, Goldenberg et al., international application publication No. WO 91/11465 (1991), Hansen et al., international application publication No. WO 93/23062, and Goldenberg, international application publication No. WO 94/04702 (1994).

Furthermore, such antibodies are readily available from commercial sources. For example, rodent monoclonal antibodies that bind with adenocarcinoma-associated antigen (Cat. No. 121730), human chorionic gonadotropin (Cat. No. 230740), carcinoembryonic antigen (Cat. Nos. 215920 and 215922), human alpha-fetoprotein (Cat. No. 341646), and the like can be obtained from Calbiochem-Novabiochem Corp. (San Diego, Calif.). Moreover, rodent monoclonal antibodies that bind with antigenic determinants of infectious agents such as *Escherichia coli* (HB 8178), *Legionella pneumophila* (CRL 1770), *Schistosoma mansoni* (HB 8088), *Streptococcus*, Group A (HB 9696), *Treponema pallidum* (HB 8134), hepatitis B (CRL 8017), herpes simplex (HB 8181), human immunodeficiency virus (HB 9101), among others, can be obtained from American Type Culture Collection (Rockville, Md.). Furthermore, murine monoclonal antibodies against merozoites and sporozoites of *Plasmodium falciparum* can be prepared as described by Goldenberg, U.S. Pat. No. 5,332,567 (1994).

An α-Gal antibody of the present invention may also be derived from a subhuman primate antibody. General techniques for raising therapeutically useful antibodies in baboons may be found, for example, in Goldenberg et al., international patent publication No. WO 91/11465 (1991), and in Losman et al., *Int. J. Cancer* 46:310 (1990).

Alternatively, a mutated antibody may be derived from a "humanized" monoclonal antibody. Humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l Acad. Sci. USA* 86:3833 (1989). Techniques for producing humanized Mabs are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), and Singer et al., *J. Immun.* 150:2844 (1993).

As an alternative, an α-Gal antibody of the present invention may be derived from human antibody fragments isolated from a combinatorial immunoglobulin library. See, for example, Barbas et al., METHODS: *A Companion to Methods in Enzymology* 2:119 (1991), and Winter et al., *Ann. Rev. Immunol.* 12:433 (1994). Cloning and expression vectors that are useful for producing a human immunoglobulin phage library can be obtained, for example, from STRATAGENE Cloning Systems (La Jolla, Calif.).

In addition, a mutated antibody of the present invention may be derived from a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994).

B. Introduction of the α-Galactosyl Epitope into Antibodies by Engineering a Glycosylation Site DNA molecules encoding suitable variable regions, constant domains, and hinge regions can be synthesized using the polymerase chain reaction with RNA from antibody-producing hybridomas that produce such antibodies. General techniques for the synthesis of antibody components are described, for example, by Orlandi et al., *Proc. Nat'l Acad. Sci. USA* 86:3833 (1989), Larrick et al., Methods: *A Companion to Methods in Enzymology* 2:106 (1991), and by Kang et al., id. at 111. Also see, Ward et al., "Genetic Manipulation and Expression of Antibodies," in MONOCLONAL ANTIBODIES: PRINCIPLES AND APPLICATIONS, pages 137–185 (Wiley-Liss, Inc. 1995), and Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166–179 (Cambridge University Press 1995).

The constant-, or "Fc-," associated carbohydrate moiety at Asn297 of the CH2 domains of antibodies is incompletely processed and varies in structure from complex- to high-mannose forms. Ip et al., *Arch. Biochem. Biophys.* 308:387 (1994); Tandai et al., *Arch. Biochem. Biophys.* 291:339 (1991). No α-galactosyl epitope has been identified in these carbohydrates. Moreover, the spatial orientation of these Fc-appended carbohydrates may also limit the accessibility of antibodies specific for these carbohydrates.

In contrast, antibodies having natural or engineered Asn-linked glycosylation sites at exposed positions, when expressed in cell lines (e.g., SP2/O) containing α-1,3galactosyl transferase, are expected to be glycosylated with the α-galactosyl epitope. For example, the VK-associated carbohydrate in murine LL2, as described by Leung et al., *Int. J. Cancer* 60:534 (1995), and Leung et al., *J. Immunol.* 154:5919 (1995), contains the α-galactosyl epitope. See Exhibit 1. This also was the case for HCN1- and HCN5-associated carbohydrates described herein. See Example 2. More than 90% of the oligosaccharides sequenced were found to contain the α-galactosyl epitope (except species N5-a).

Computer modeling studies and conjugation studies indicate that the HCN1 and HCN5 carbohydrates are located at highly exposed positions. Binding of these carbohydrates to chelates or large molecules such as 18 kD dextran-doxorubicin complexes did not seem to affect immunoreactivity, indicating that these sites are amenable for complex formation with anti-Gal while tightly associated with their target antigens. See Example 2.

The use of any glycosylation site, natural or engineered, should have the following characteristics:

i. all or most of the associated carbohydrates should contain the α-galactosyl epitope;

ii. α-galactosyl epitopes must be located at exposed positions for easy access of anti-Gal; and iii. the attached carbohydrates should be at a suitable distance from the antigen binding site so that binding of anti-Gal at the associated carbohydrates does not affect, or has minimal effects, on the targeting ability of the therapeutic α-Gal antibody.

It may be advantageous to include more than one type of engineered glycosylation site in the same antibody. For example, hLL2 can be engineered with both a VK-appended glycosylation site and an HCN5 glycosylation site. According to experimental results described herein (FIGS. 5 and 6), both glycosylation sites should contain the α-galactosyl epitope. Thus, one molecule of whole IgG of F(ab')$_2$ should contain four α-galactosyl epitopes, which would allow the binding of at least two anti-Gal antibodies. Furthermore, the binding of at least two anti-Gal antibodies would bring at least two Fc fragments to close proximity for the binding and activation of C1q molecules, resulting in complement activation.

Engineering glycosylation sites can be achieved by the introduction of the consensus glycosylation sequence, Asn-X-Ser/Thr, into the desired positions by site-directed mutagenesis. General methodology for engineering glycosylation sites is described by Hansen et al., U.S. Pat. No. 5,443,953 (1995), and by Leung et al., *J. Immunol.* 154:5919 (1995). Routine experimentation will be required to determine whether a particular glycosylation site is useful for the present invention. The composition of attached oligosaccharides can be determined using standard techniques such as SDS-PAGE, carbohydrate staining and fluorophore-assisted carbohydrate electrophoresis (FACE). The topographical locations of these sites, once identified, can also be determined with the aid of computer modeling.

C. Methods for Expressing and Isolating the Protein Product of a Mutated Antibody DNA Sequence To express the polypeptide encoded by the mutated antibody DNA sequence, the DNA sequence must be operably linked to regulatory sequences controlling transcriptional expression in an expression vector and then, introduced into either a prokaryotic or eukaryotic host cell. In addition to transcriptional regulatory sequences, such as promoters and enhancers, expression vectors include translational regulatory sequences and a marker gene which is suitable for selection of cells that carry the expression vector.

Suitable promoters for expression in a prokaryotic host can be repressible, constitutive, or inducible. Suitable promoters are well-known to those of skill in the art and include promoters capable of recognizing the T4, T3, Sp6 and T7 polymerases, the $P_R$ and $P_L$ promoters of bacteriophage lambda, the trp, recA, heat shock, and lacZ promoters of *E. coli*, the α-amylase and the $\sigma^{28}$-specific promoters of *B. subtilis*, the promoters of the bacteriophages of Bacillus, Streptomyces promoters, the int promoter of bacteriophage lambda, the bla promoter of the β-lactamase gene of pBR322, and the CAT promoter of the chloramphenicol acetyl transferase gene. Prokaryotic promoters are reviewed by Glick, *J. Ind. Microbiol.* 1:277 (1987); Watson et al., MOLECULAR BIOLOGY OF THE GENE, 4th Ed., Benjamin Cummins (1987); Ausubel et al., supra, and Sambrook et al., supra.

A preferred prokaryotic host is *E. coli*. Preferred strains of *E. coli* include Y1088, Y1089, CSH18, ER1451, and ER1647 (see, for example, Brown (Ed.), MOLECULAR BIOLOGY LABFAX, Academic Press (1991)). An alternative preferred host is *Bacillus subtilus*, including such strains as BR151, YB886, MI119, MI120, and B170 (see, for example, Hardy, "Bacillus Cloning Methods," in DNA CLONING: A PRACTICAL APPROACH, Glover (Ed.), IRL Press (1985)).

Methods for expressing antibodies in prokaryotic hosts are well-known to those of skill in the art. See, for example, Ward et al., "Genetic Manipulation and Expression of Antibodies," in MONOCLONAL ANTIBODIES: PRINCIPLES AND APPLICATIONS, pages 137–185 (Wiley-Liss, Inc. 1995). Moreover, expression systems for cloning antibodies in prokaryotic cells are commercially available. For example, the IMMUNO ZAP™ Cloning and Expression System (Stratagene Cloning Systems; La Jolla, Calif.) provides vectors for the expression of antibody light and heavy chains in E. coli.

The mutated antibody is preferably expressed in eukaryotic cells, and especially mammalian, insect, and yeast cells. Especially preferred eukaryotic hosts are mammalian cells. Mammalian cells provide post-translational modifications to the cloned polypeptide including proper folding and glycosylation. For example, such mammalian host cells include COS-7 cells (ATCC CRL 1651), non-secreting myeloma cells (SP2/0-AG14; ATCC CRL 1581), rat pituitary cells (GH$_1$; ATCC CCL 82), and rat hepatoma cells (H-4-II-E; ATCC CRL 1548).

Especially preferred mammalian cells contain α1,3galactosyl transferase, which is the enzyme that mediates the introduction of the α-galactosyl epitope. As noted above, the enzyme should be expressed by cells from all mammalian species, excluding humans and other old World primates.

Nevertheless, it may be desirable to introduce α1,3galactosyl transferase enzyme activity into cells that normally lack the enzyme, or to augment the level of α1,3galactosyl transferase activity in cells that contain the α1,3galactosyl transferase gene. Accordingly, cell lines that express a foreign α1,3galactosyl transferase gene can be produced using the general methods of transfection described herein. Examples of suitable α1,3galactosyl transferase-encoding sequences that have been cloned include DNA molecules that code for murine, bovine, porcine and marmoset α1,3galactosyl transferases. Larsen et al., *Proc. Nat'l Acad. Sci. USA* 86:8227 (1989), Joziasse et al., *J. Biol. Chem.* 264:14290 (1989), Joziasse et al., *J. Biol. Chem.* 267:5534 (1992), Strahan et al., *Immunogenet.* 41:101 (1995), and Galili et al., international publication No. WO 95/24924.

For a mammalian host, the transcriptional and translational regulatory signals may be derived from viral sources, such as adenovirus, bovine papilloma virus, and simian virus. In addition, promoters from mammalian expression products, such as actin, collagen, or myosin, can be employed. Alternatively, a prokaryotic promoter (such as the bacteriophage T3 RNA polymerase promoter) can be employed, wherein the prokaryotic promoter is regulated by a eukaryotic promoter (for example, see Zhou et al., *Mol. Cell. Biol.* 10:4529 (1990); Kaufman et al., *Nucl. Acids Res.* 19:4485 (1991)). Transcriptional initiation regulatory signals may be selected which allow for repression or activation, so that expression of the genes can be modulated.

In general, eukaryotic regulatory regions will include a promoter region sufficient to direct the initiation of RNA synthesis. Such eukaryotic promoters include the promoter of the mouse metallothionein I gene (Hamer et al., *J. Mol. Appl. Gen.* 1:273 (1982)); the TK promoter of Herpes virus (McKnight, *Cell* 31:355 (1982)); the SV40 early promoter (Benoist et al., *Nature* (London) 290:304 (1981)); the Rous sarcoma virus promoter (Gorman et al., supra); the cytomegalovirus promoter (Foecking et al., *Gene* 45:101 (1980)); the yeast gal4 gene promoter (Johnston, et al., *Proc. Natl. Acad. Sci. (USA)* 79:6971 (1982); Silver, et al., *Proc. Natl. Acad. Sci. (USA)* 81:5951 (1984)); and the IgG promoter (Orlandi et al., *Proc. Natl. Acad. Sci. USA* 86:3833 (1989)).

Strong regulatory sequences are the most preferred regulatory sequences of the present invention. Examples of such preferred regulatory sequences include the SV40 promoter-enhancer (Gorman, "High Efficiency Gene Transfer into Mammalian cells," in DNA CLONING: A PRACTICAL APPROACH, Volume II, Glover (Ed.), IRL Press pp. 143–190 (1985)), the hCMV-MIE promoter-enhancer (Bebbington et al., *Bio/Technology* 10:169 (1992)), and antibody heavy chain promoter (Orlandi et al., *Proc. Natl. Acad. Sci. USA* 86:3833 (1989)). Also preferred are the kappa chain enhancer for the expression of the light chain and the IgH enhancer (Gillies, "Design of Expression Vectors and Mammalian Cell Systems Suitable for Engineered Antibodies," in ANTIBODY ENGINEERING: A PRACTICAL GUIDE, C. Borrebaeck (Ed.), W. H. Freeman and Company, pp. 139–157 (1992); Orlandi et al., supra).

The mutated antibody-encoding sequence and an operably linked promoter may be introduced into eukaryotic cells as a non-replicating DNA molecule, which may be either a linear molecule or, more preferably, a closed covalent circular molecule. Since such molecules are incapable of autonomous replication, the expression of the protein may occur through the transient expression of the introduced sequence. Preferably, permanent expression occurs through the integration of the introduced sequence into the host chromosome.

Preferably, the introduced sequence will be incorporated into a plasmid or viral vector that is capable of autonomous replication in the recipient host. Several possible vector systems are available for this purpose. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired genomic or cDNA sequences into the host chromosome. Additional elements may also be needed for optimal synthesis of mRNA. These elements may include splice signals, as well as transcription promoters, enhancers, and termination signals. The cDNA expression vectors incorporating such elements include those described by Okayama, *Mol. Cell. Biol.* 3:280 (1983), Sambrook et al., supra, Ausubel et al., supra, Bebbington et al., supra, Orlandi et al., supra, and Fouser et al., *Bio/Technology* 10:1121 (1992); Gillies, supra. Genomic DNA expression vectors which include intron sequences are described by Orlandi et al., supra. Also, see generally, Lerner et al. (Eds.), NEW TECHNIQUES IN ANTIBODY GENERATION, *Methods* 2(2) (1991).

In order to obtain mammalian cells that express intact antibody, an expression vector comprising an antibody light chain can be co-transfected into mammalian cells with a mutated antibody heavy chain expression vector. See, for example, Orlandi et al., supra. Alternatively, mammalian cells containing a mutated heavy chain expression vector can be transfected with an expression vector comprising an antibody light chain, and mammalian cells containing an expression vector comprising a light chain can be transfected with a mutated heavy chain expression vector. Moreover, mammalian cells can be transfected with a single expression vector comprising DNA fragments that encode an antibody light chain, as well as DNA fragments that encode mutated antibody heavy chain. See, for example, Gillies, supra; Bebbington et al., supra. Any of these approaches will produce transfected cells that express whole antibody molecules that have an engineered glycosylation site. Standard transfection techniques are well known in the art. See, for example, Sambrook et al., supra; Ausubel et al., supra.

D. Methods for Isolating a Mutated Antibody from Transfected Cells

Transfected cells that carry the expression vector are selected using the appropriate drug. For example, G418 can be used to select transfected cells carrying an expression vector having the aminoglycoside phosphotransferase gene. Southern et al., *J. Mol. Appl. Gen.* 1:327 (1982). Alternatively, hygromycin-B can be used to select transfected cells carrying an expression vector having the hygromycin-B-phosphotransferase gene. Palmer et al., *Proc. Natl. Acad. Sci. USA* 84:1055 (1987). Alternatively, aminopterin and mycophenolic acid can be used to select transfected cells carrying an expression vector having the xanthine-guanine phosphoribosyltransferase gene. Mulligan et al., *Proc. Natl. Acad. Sci. USA* 78:2072 (1981).

Another example of a suitable expression system is the pdHL2 vector, which has an amplifiable murine dhfr gene that allows subsequent selection and amplification by methotrexate treatment. Gillies et al., *J. Immunol. Methods* 125:191 (1989). The pdHL2 vector provides expression of both IgG heavy and light chain genes that are independently controlled by two metallothionine promoters and IgH enhancers.

As an illustration, SP2/0 cells can be transfected by electroporation with linearized pdHL2 vector that contains coding sequences for mutated antibody components. Selection can be initiated 48 hours after transfection by incubating cells with medium containing 0.05–0.1 µM methotrexate. Amplification of mutated antibody sequences is achieved by a stepwise increase in methotrexate concentration up to 5 µM.

Transfected cells that produce a mutated antibody can be identified using a variety of methods. For example, any immunodetection assay can be used to identify such "transfectomas."

After transfectomas have been identified, the cells are cultured and antibodies are isolated from culture supernatants. Isolation techniques include affinity chromatography with Protein-A Sepharose, size-exclusion chromatography, and ion-exchange chromatography. For example, see Coligan et al. (eds.), CURRENT PROTOCOLS IN IMMUNOLOGY, John Wiley & Sons (1991), for detailed protocols.

E. Methods for Introducing the α-Galactosyl Epitope into Antibodies by In Vitro Enzymatic Modification (1) Enzymatic Modification of Natural Oligosaccharide Chains In vitro enzymatic treatment can be used to alter the carbohydrate composition of oligosaccharide chains in Mabs that lack an α-galactosyl epitope. For example, a preparation of Mabs can be treated with recombinant α1,3galactosyl transferase. Routine experimentation may be required to determine whether a particular Mab preparation requires pretreatment with sialidase to expose N-acetyllactosamine acceptors. General techniques for introducing the α-galactosyl epitope by in vitro enzyme treatment are described, for example, by Galili et al., *Glycobiology* 5:775 (1995), and by LaTemple et al., *Cancer Res.* 56:3069 (1996).

(2) Conjugation of Synthetic Oligosaccharides Containing Single or Multiple Repeats of the α-Galactosyl Epitope Designer carbohydrates can be custom-made to contain either a single copy or multiple repeats of the α-galactosyl epitope. These synthetic oligosaccharides can be chemically or enzymatically conjugated to antibodies using conventional conjugation methods, either randomly, or most preferably, site-specifically.

α-Galactosyl epitope-containing sugars can be conjugated to CH2-appended carbohydrates and to other natural or engineered carbohydrates that meet the criteria set forth above, using standard techniques. Shih et al., *Int. J. Cancer* 41:832 (1988); Shih et al., *Cancer Immunol. Immunother.* 31:197 (1990a); Shih et al., *Int. J. Cancer* 46:1101 (1990b); Shih et al., *Cancer Res.* 51:5192 (1991). The presence of multiple repeats of the α-galactosyl epitope should stimulate multimeric binding of anti-Gal which subsequently will enhance C1q binding and activation, as well as phagocytosis by antigen presenting cells.

4. Prevention of Early Complex Formation of Targeting Agent Armed With the α-Galactosyl Epitope by Anti-Gal Neutralization by endogenous anti-Gal will decrease the efficacy of α-Gal antibodies. There are at least three ways to overcome this potential problem.

A. Use of Monomeric Fab or Fab' Fragments

Figure 3:
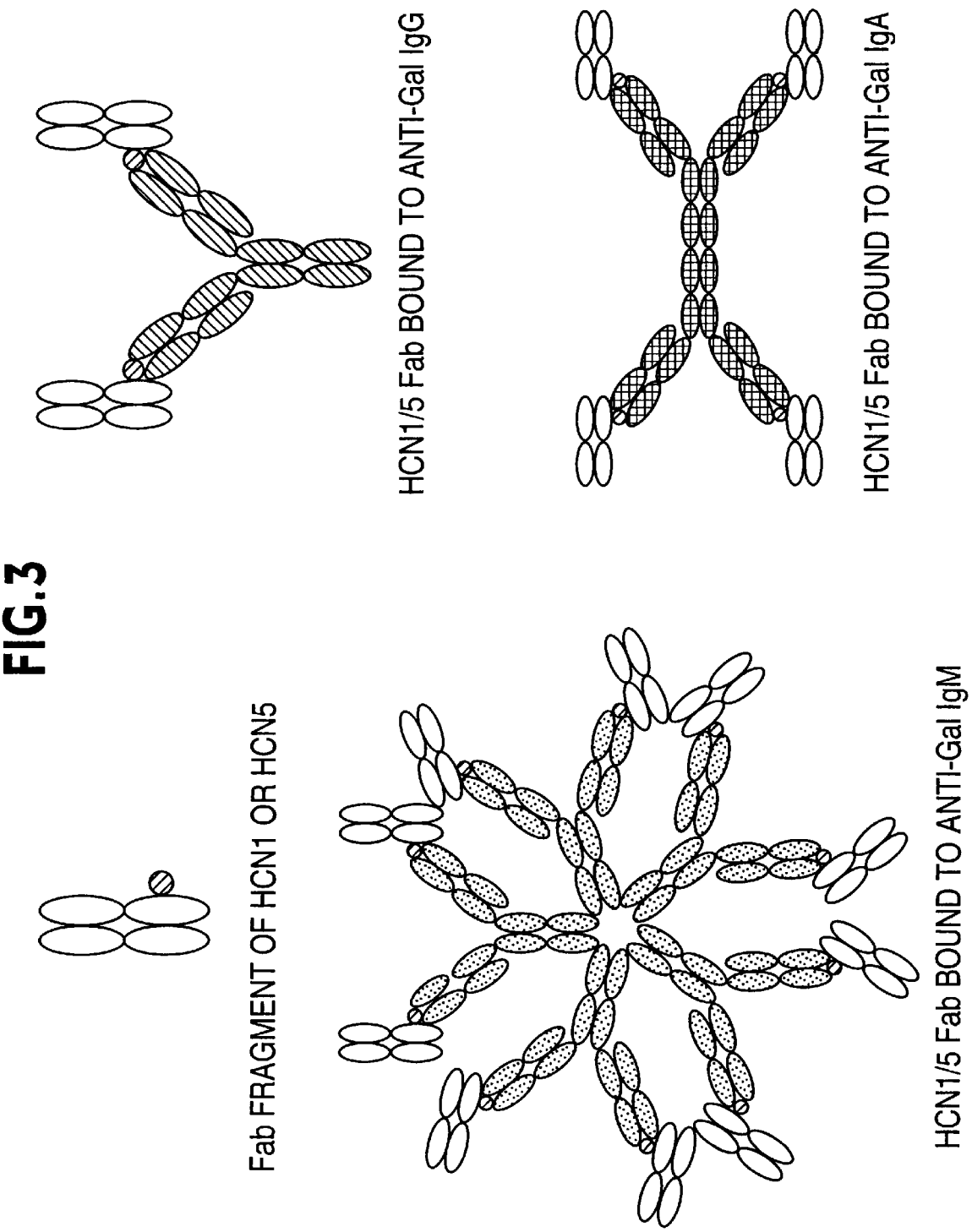
FIG. 3 portrays immunoglobulin complex formations expected with an Fab fragment of hLL2HCN1 or hLL2HCN5 with IgG, IgA and IgM anti-Gal.

As discussed above, experimental results indicate the presence of adjacent α-galactosyl epitopes on each mutated experimental antibody. It is possible that, due to steric hindrance, one anti-Gal can only react to one α-galactosyl epitope in each engineered carbohydrate. That is, a bivalent anti-Gal IgG can only bind to a maximum of two molecules of α-Gal-Fab or α-Gal-Fab'. See FIG. 3. Since the α-galactosyl epitope is deliberately positioned away from the antigen binding site, the targeting specificity and affinity of the α-Gal-Fab or α-Gal-Fab' should not be affected. This should be true even when the multimeric IgM and IgA are taken into consideration. See FIG. 3. In fact, the presence of this immunoreactive multimeric structure might be advantageous in some cases, as this will enhance binding of the antibody fragment, now in multivalent form, to the target antigen.

B. Pretreatment to Clear Endogenous Anti-Gal

Cooper et al., *Transplant. Proc.* 24:566 (1992), neutralized anti-blood group A and B antibodies in vivo using synthetic blood group A or B trisaccharides. This treatment resulted in the delay, and in some cases elimination of, rejection of ABO-mismatched allogeneic heart transplants in baboons.

Similarly, synthetic free α-galactosyl epitope, or related oligosaccharides have been demonstrated to be effective in inhibiting anti-Gal binding to porcine endothelial cells and to prevent >90% of antibody binding. Galili et al., *J. Exp. Med.* 160:1519 (1996). Moreover, Neethling et al., *Transplantation* 57:959 (1994), used αGal oligosaccharides to protect pig kidney (PK15) cells from the cytotoxic effect of anti-pig antibodies.

These observations indicate the possibility of using synthetic oligosaccharides to induce a brief window for α-Gal antibody to locate the target sites. When the titer of circulating anti-Gal returns to normal, the anti-Gal can act on the surface-bound α-Gal antibody on the target sites and initiate complement attack or other immune responses against the target cells.

Accordingly, the therapeutic $\alpha$-Gal antibody can be administered in the presence of high concentrations of synthetic oligosaccharides for two to six hours, for example, after the administration of high doses of neutralizing sugars. In addition to synthetic $\alpha$-galactosyl epitope and multimers thereof, suitable inhibitory molecules include melibiose, Galα1-6Gal, Galα1-3Gal, Galα1-3Galβ1-O-methyl, Galα1-3Galβ1-p-nitrophenyl, Galα1-3Galβ1-4GlcNAc-O-benzyl, Galα1-3Galβ1-4Glc, and Galα1-3Galβ1-3GlcNAcβ-benzyl. See, for example, Galili et al., *Transplantation* 62:256 (1996).

An alternative approach is suggested by the observation that circulating anti-Gal clears immediately after anastomosis of xenografts, which served as a sink for the antibodies. Similarly, anti-Gal can be removed by serum adsorption before the therapeutic α-Gal antibody is injected into the subject.

C. Controlled Release of Protected α-Galactosyl Epitope

Endogenous neuraminidases are present in circulation, causing desialylation as glycoproteins "age." Desialylated proteins are removed for destruction by the Kupffer cells in the liver. Carbohydrate sequencing data on the HCN1- and HCN5-appended oligosaccharides revealed the possible sialylation of the α-galactosyl epitope. See Example 2. Since sialylation might shield the α-galactosyl epitope from being recognized by anti-Gal, desialylation might be needed to expose the epitopes if they are to react with the anti-Gal. Endogenous desialylation of sialic acid or sialic acid conjugated with a protecting group may be sufficient to deprotect the bound α-Gal antibody to effect hyperacute rejection or immune responses mediated by anti-Gal. However, deprotection can also be controlled by the infusion of neuraminidase for sialic acid removal. Other methods of protection/deprotection, either chemically or enzymatically, can be used to control the proper timing of exposure of α-galactosyl epitope.

5. Use of α-Gal Antibodies for Therapy

In general, the dosage of administered α-Gal antibodies will vary depending upon such factors as the patient's age, weight, height, sex, general medical condition and previous medical history. Preferably, a saturating dose of α-Gal antibody is administered to a patient. It is possible to provide such high doses of α-Gal antibodies because the antibodies are not conjugated with radionuclides or cytotoxic agents. α-Gal antibodies can be administered as whole IgG, F(ab')₂, F(ab)₂ Fab' or Fab.

Typically, it is desirable to provide the recipient with a dosage of antibody that is in the range of from about 50 to 500 milligrams of α-Gal antibody, although a lower or higher dosage also may be administered as circumstances dictate. As discussed above, high doses of α-Gal antibody may cause anaphylaxis due to complement activation with endogenous α-Gal antibodies. This side effect, however, can be prevented by administration of oligosaccharides that bind with endogenous α-Gal antibodies, as detailed below.

Administration of α-Gal antibodies to a patient can be intravenous, intraarterial, intraperitoneal, intramuscular, subcutaneous, intrapleural, intrathecal, by perfusion through a regional catheter, or by direct intralesional injection. When administering α-Gal antibodies by injection, the administration may be by continuous infusion or by single or multiple boluses.

The α-Gal antibodies of the present invention can be formulated according to known methods to prepare pharmaceutically useful compositions, whereby antibodies are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 19th Ed. (Mack Publishing Co. 1995), and GILMAN'S THE PHARMACOLOGICAL BASIS OF THERAPEUTICS, 7th Ed. (MacMillan Publishing Co. 1985).

For purposes of therapy, an α-Gal antibody and a pharmaceutically acceptable carrier are administered to a patient in a therapeutically effective amount. A combination of an α-Gal antibody and a pharmaceutically acceptable carrier is said to be administered in a "therapeutically effective amount" if the amount administered is physiologically significant. An agent is physiologically significant if its presence results in a detectable change in the physiology of a recipient patient. In the present context, an agent is physiologically significant if its presence results in the inhibition of the growth of target cells.

As discussed above, it may be desirable either to pretreat a subject with oligosaccharides that bind with endogenous anti-Gal antibodies or to administer such oligosaccharides with therapeutic α-Gal antibodies. The dosage of oligosaccharides will vary depending upon the particular patient and upon the molecular size of the administered oligosaccharide. Carbohydrates containing the α-galactosyl epitope can be injected as an intermittent bolus or by infusion. Based upon the studies of Cooper et al., *Transplantation Proceeding* 24:556 (1992), the half-life of injected carbohydrates of similar composition was estimated to be less than two hours. Intermittent bolus injection can be performed at 0, 1, 2, 4, 8 and/or 14 hours before and/or after the injection of therapeutic α-Gal antibodies, at dosages of 100–200 mg oligosaccharide per kilogram body weight. Alternatively, neutralizing oligosaccharides can be infused, for example, at a rate of 300–500 mg/hour. Infusion can begin 0–10 hours before the administration of therapeutic α-Gal antibodies, and infusion can continue when necessary to allow therapeutic α-Gal antibodies to bind to target cells. No adverse effects were observed when carbohydrates were administered to patients using the similar protocols of Cooper et al.

Oligosaccharides are administered with a pharmaceutically acceptable carrier in a "therapeutically effective amount." The amount of oligosaccharides administered is a therapeutically effective amount if the oligosaccharides increase the efficacy of α-Gal antibodies by binding with endogenous anti-Gal.

6. Use of Other Epitopes as a Substitute for the α-Galactosyl Epitope

Depending on the blood group of the individuals, pre-existing levels of anti-blood group antibody might exist in circulation. That is, a person with blood type A may have anti-B antibodies, a person with blood type B may have anti-A antibodies, and a person with blood type O may have both anti-B and anti-A antibodies. This has imposed problems in organ allotransplantation across the ABO blood group barrier, resulting in significant reduction in graft survival. However, it is possible to take advantage of such sensitization by producing herapeutic antibodies comprising a blood group ligosaccharide. According to this approach to immunotherapy, therapeutic antibody conjugated with the appropriate blood group antigen (e.g., B trisaccharide for a subject having blood type A or O) is injected into the subject following pretreatment with blocking trisaccharides. When the level of reactive anti-blood group antigen returns to normal, ADCC and CDCC-type rejection will take place as described earlier.

Alternatively, subjects can be pre-immunized with the appropriate blood group antigens to enhance anti-blood group antibodies. That is, a patient with blood type A is immunized with B antigen, and vice versa. The level of anti-blood group antibody in circulation is then monitored until it reaches a predetermined level (e.g., >1:500), and then, therapeutic antibodies conjugated with the appropriate blood group antigen and blocking trisaccharides are administered as described above.

More generally, the approach to immunotherapy described herein can be achieved using any antigen other than the α-galactosyl epitope. That is, a patient can be immunized with an antigen, such as an oligosaccharide, peptide, hapten, or similar molecule ("the sensitizing epitope"). When serum antibodies to the sensitizing epitope exceeds 1% of total circulating IgGs, the subject can be treated with antibodies that bind with a disease-associated antigen and that contain the sensitizing epitope. Prior to such treatment, however, circulating anti-sensitizing epitope antibodies can be temporarily cleared by injection of saturating quantities of sensitizing epitope into the blood stream. The anti-sensitizing epitope antibodies should be able to react with the target-bound antibodies and mediate complement activation and opsonization similar to that achieved with the α-galactosyl epitope and anti-Gal, as described above.

7. Use of the α-Galactosyl Epitope Attached to Other Targeting Agents

The α-galactosyl epitope, engineered enzymatically or chemically, can be conjugated to a variety of targeting agents. These targeting agents can be peptides such as somatostatin and vasoactive intestinal peptide, or they can be small molecules and mimetics that exhibit targeting abilities. For example, studies indicate that high-affinity somatostatin (SRIF) (SEQ ID No:4) receptors are expressed in a variety of human tumors, including neuroendocrine tumors, small cell lung cancer, lymphomas, and breast tumors. Accordingly, radiolabeled octreotide analogues of somatostatin have been used for tumor diagnosis. Kreening et al., *Eur. J. Nucl. Med.* 20: 283 (1993). Thus, octreotide analogues can be conjugated with α-galactosyl epitopes and used to target tumors that overexpress high-affinity SRIF receptors.

The present invention, thus generally described, will be understood more readily by reference to the following examples, which are provided by way of illustration and are not intended to be limiting of the present invention.

EXAMPLE 1
Detection of the α-Galactosyl Epitope in Murine LL2 Antibody and in Humanized Fragments of the LL2 Antibody LL2 is a murine monoclonal antibody (mLL2) that has been shown to be effective for the diagnosis and treatment of non-Hodgkins B-cell lymphoma. Goldenberg et al., *J. Clin. Oncol.* 9:548 (1991); Murthy et al., *Eur. J. Nucl. Med.* 19:394 (1992). Nucleotide sequence analysis of the mLL2 variable region led to the identification of a glycosylation site in the framework-1 (FR1) sequence of the kappa light-chain variable region (VK). Leung et al., *Int. J. Cancer* 60:534 (1995). Experiments were performed to determine whether the VK-appended carbohydrate contains an α-galactosyl epitope in mLL2, in humanized LL2 (hLL2), and in hLL2 having a grafted VK-appended glycosylation site (hLL2N). Construction of humanized LL2 antibodies is described by Leung et al., *Mol. Immunol.* 32:1413 (1995).

In these studies, the presence of the α-galactosyl epitope was determined by measuring the binding of biotinylated *B. simplicifolia IB₄* lectin ("BS lectin"), which binds specifically with α-galactosyl epitopes. Wood et al., *Arch. Bio-chem. Biophys.* 198:1 (1979). IB4 lectin was purchased from Vector Laboratories (Burlingame, Calif.) and was biotinylated using standard techniques. Briefly, antibodies were coated on ELISA plates using solutions containing 1.25–10 μg antibody/ml. A 1% solution of bovine serum albumin was used to block nonspecific binding sites. Biotinylated IB4 was added to the antibody-coated wells, and the mixtures were incubated. After washing the wells, horseradish peroxidase-streptavidin was added, and the binding of IB4 to bound antibodies was detected following addition of peroxidase substrates.

Figure 5:
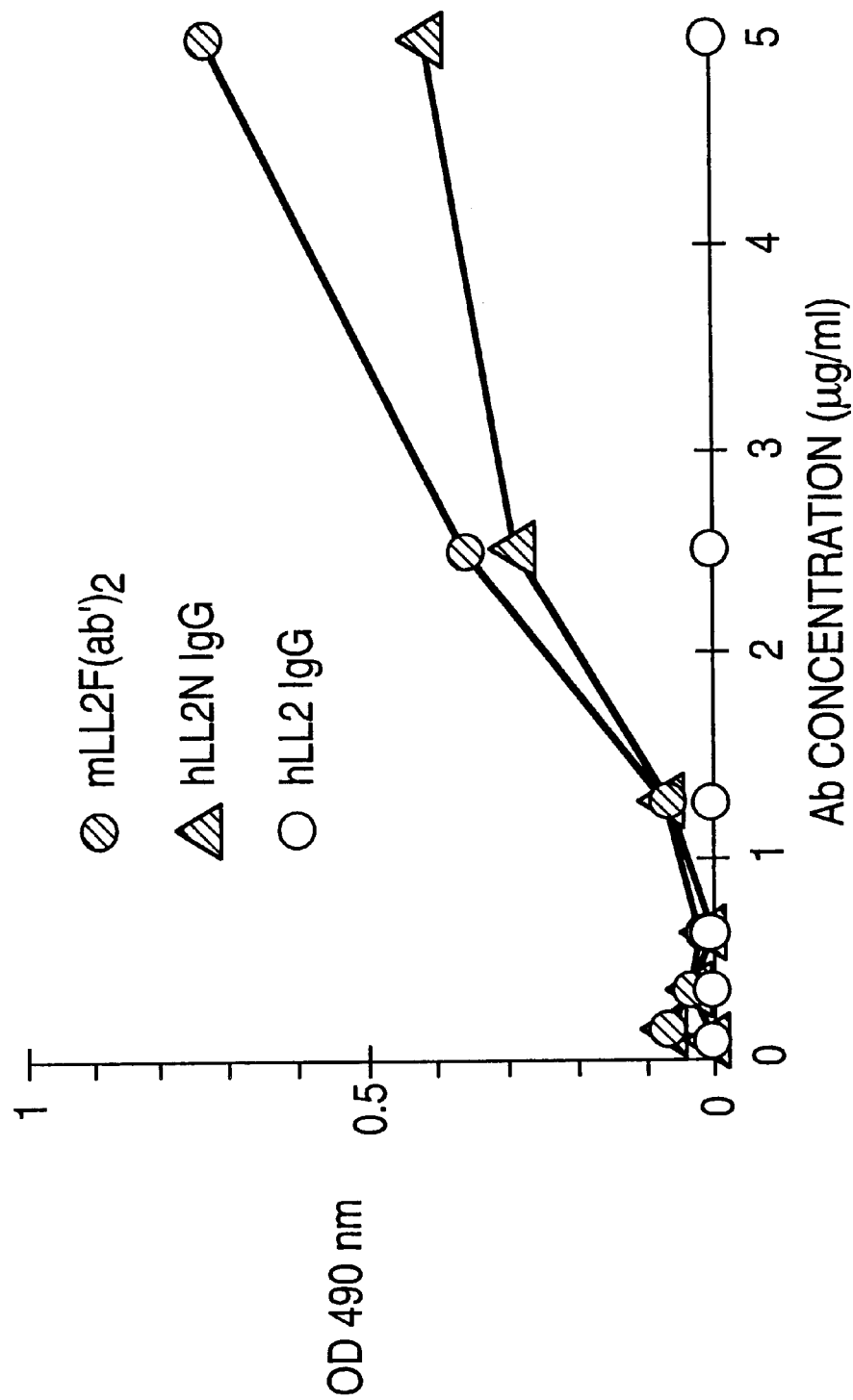
FIG. 5 shows the results of an enzyme-linked immunosorbent assay (ELISA) used to detect the presence of the α-galactosyl epitope in the VK-appended carbohydrates in murine LL2 (mLL2) antibody, whole humanized LL2 (hLL2) antibody that contains the VK-appended carbohydrate (hLL2N), and hLL2 that does not contain the VK-appended carbohydrate.

As shown in FIG. 5, IB4 bound to mLL2 in a dose-dependent manner. IB4 also bound to hLL2N, which contains the mLL2 VK-appended glycosylation site. These results indicate the presence of α-galactosyl epitopes in the VK-appended carbohydrates of mLL2 and hLL2N. Thus, mLL2, chimeric mLL2 antibodies, humanized LL2, and other antibodies which contain the kappa light-chain variable region of mLL2, can be produced as therapeutic antibodies that contain at least one α-galactosyl epitope.

In contrast, FIG. 5 shows that IB4 did not bind to hLL2 that lacked the mLL2 VK-appended glycosylation site. Since whole hLL2 antibody contains only CH2-appended carbohydrate, this observation indicates that the CH2-appended carbohydrate does not contain an α-galactosyl epitope.

EXAMPLE 2
Introduction of the α-Galactosyl Epitope into Antibodies

N-linked glycosylation sites were engineered into the human heavy chain constant regions (CH1 domain) of hLL2 antibody. Methods for construction, expression, production and purification of N-linked glycosylation mutant Mabs have been described by Hansen et al., U.S. Pat. No. 5,443, 953 (1995), and by Leung et al., *J. Immunol.* 154:5919 (1995).

Mutant antibodies hLL2HCN1 and hLL2HCN5 were selected from a battery of hLL2 variants, each of which were engineered with a tripeptide acceptor sequence (Asn-X-Ser/Thr) for N-linked glycosylation in the CH1 domain. Glycosylation of the HCN1 site in hLL2HCN1 is at Asn162 (NSS) in the human IgG1 CH1 domain, which is located in the middle of the β-strand C. See FIG. 1. The HCN5 site of hLL2HCN5 lies in the loop between the β-stands E and F, and glycosylation is at Asn198 (NGT). Designation of the N-glycosylation sites follows the number system of Kabat et al., SEQUENCES OF PROTEINS OF IMMUNOLOGICAL INTEREST (U.S. Government Printing Office 1991).

To prepare F(ab')₂ fragments for analysis, a solution of purified Mabs (2 mg/ml in 0.05 M sodium citrate, pH 3.4) with 10% glycerol was digested with 10 μg/ml of pepsin (Worthington, Freehold, N.J.) at 37° C. The extent of digestion was monitored by HPLC. At the completion of digestion (approximately 10 min), the reaction was terminated by the addition of 1/10 volume of 1 M Tris (pH 8.0) to the reaction mixture. The reaction mixture was passed through a protein A column and F(ab')₂ fragments were then purified from a Sepharose S column (Pharmacia, Uppsala, Sweden).

When F(ab')₂ fragments of these antibodies were analyzed on SDS-PAGE under reducing conditions, their Fd fragments showed reduced mobility when compared with that of hLL2 F(ab')₂, indicating these sites were glycosylated. The apparent molecular size for the Fd fragment of HCNS appeared to be larger than that of HCN1, suggesting a larger HCN5-appended carbohydrate moiety.

To quantitatively evaluate the sizes of these CH1-appended oligosaccharides, F(ab')₂ fragments of hLL2, hLL2HCN1 and hLL2HCN5 were prepared and subjected to mass spectrometry analysis (Mass Consortium, San Diego, Calif.). The mass spectrometry-measured molecular mass of the F(ab')$_2$ fragments of hLL2, hLL2HCN1 and hLL2HCN5 were 99,471, 102,884 and 104,345, respectively. Since the Fc portion containing the CH2-appended carbohydrate was excluded, the mass difference between the F(ab')$_2$ fragments of non-glycosylated hLL2 and the glycosylation mutants should represent the mass of the engineered, CH1-appended carbohydrates. Therefore, the molecular sizes of HCN1- and HCN5-appended carbohydrates were calculated to be about 3,400 and 4,900 daltons, respectively. Taking the molecular weight of an average monosaccharide residue to be 240, the HCN5-appended carbohydrate should contain three to four more monosaccharide residues than those attached to the HCN1 site. Structural analysis of the engineered carbohydrates showed this to be the case.

The structures of the CH1-appended carbohydrates of hLL2HCN1 an hLL2HCN5 were determined using FACE, which involves releasing, separating, quantifying and sequencing complex oligosaccharides from glycoproteins. Starr et al., *J. Chromatogr. A* 720:295 (1996). In these studies, the N-linked oligosaccharides were released from 200 μg of denatured (0.2% SDS, 100 mM β-mercaptoethanol, boiled for 3 min) F(ab')$_2$ fragments by reacting with two units of peptide N-glycosidase F (PNGase F; Boehringer Mannheim, Indianapolis, Ind.) in 0.1 M potassium phosphate buffer (pH 7.0) with 2% NP-40 at 37° C. for 16 hours. The released oligosaccharides were then labeled with the fluorophore 8-aminonaphthalene-1,3,6-trisulfonic acid (ANTS) using an N-linked oligosaccharide profiling kit according to the manufacturer's specifications (Bio-Rad, Hercule, Calif.). The apparent size of each ANTS-oligosaccharide in polyacrylamide gel was estimated from glucose oligomer ladder standards and expressed as degree of polymerization (DP). Individual ANTS-labeled oligosaccharide species were isolated from precast polyacrylamide gels (Bio-Rad) and further sequenced by sequential digestion with combinations of exoglycosidases, including: N-acetylneuraminidase III (NANaseIII, which cleaves α2-3, 6,8 linked N-acetylneuraminic acids), β-galactosidase III (GALaseIII, which is specific for β1-4 linked galactose), galactosidase α (GALaseα, which is α1-3 linked galactose-specific), hexosidase III (HEXaseIII, which hydrolyzes β1,-2,3,4,6 linked N-acetylglucosamine), mannosidase II (MANaseII, which cleaves α1-2,3,6 linked mannose) and fucosidase I (FUCaseI, which is α1-6 linked fucose-specific), using conditions suggested in the FACE N-linked oligosaccharide sequencing kit (Bio-Rad and Glyco, Novato, Calif.). The ANTS-oligosaccharide band shifts resulting from exoglycosidase digestion were compared to the reference data provided in the protocol menu (Bio-Rad). Interpretation of the results was based on the following guidelines: removal of a sialic acid (Sia) residue causes an upward shift of 1 DP (+1) and removal of one residue of galactose (Gal), N-acetylglucosamine (GlcNAc), mannose (Man) or fucose (Fuc) results in a downshift of −1, −0.75, −0.6 and −0.6 DP unit, respectively.

After N-linked oligosaccharides were released from hLL2HCN1 or hLL2HCN5 by PNGase F digestion, released molecules were purified and labeled with ANTS at the free reducing end. Since one molecule of ANTS attaches to one molecule of oligosaccharide, the relative amount of different carbohydrate species can be accurately determined after fractionation in a high concentration polyacrylamide gel.

Heterogenous populations of oligosaccharides were released from the F(ab')$_2$ fragments of hLL2HCN1 and hLL2HCN5. The CH1-appended carbohydrates isolated from the F(ab')$_2$ of hLL2HCN1 appeared in the FACE gel as multiple bands. Two major oligosaccharide species with apparent molecular sizes of 7.3 and 10.2 DP were designated as N1-b and N1-c, respectively. Similarly, ultiple species were found among the oligosaccharides from the HCN5 site and the three major species were designated as N5-b1 (7.3 DP), N5-b2 (7.6 DP) and N5-c (10 DP).

It was noted that the profile of HCN5 oligosaccharides was very different from that of HCN1. For example, while N1-b was the most abundant species, accounting for 55% of all labeled oligosaccharides from the HCN1 site, N5-b1, which co-migrated with and was considered equivalent to N1-b, accounted for less than 20% of the labeled HCN5 oligosaccharides. These two oligosaccharides were later shown to have identical structures. Over 60% of the HCN5 oligosaccharides were of the species N5-b2 and N5-c, each of which contained an extra outer branch composed of Sia, Gal(s) and GlcNAc. To examine and compare structural similarities or differences between HCN1- and HCN5-appended oligosaccharides, all major ANTS-oligosaccharide species, N1-b, N1-c, N5-b1, N5-b2 and N5-c, as well as minor HCN5 species N5-a (6.0 DP, 6.5%), were isolated for sequencing.

Most commonly found N-linked carbohydrates that are extensively processed in vivo are complex-type chains which contain either two, three or four outer branches extending from the common pentasaccharide core, Manα1-3 (Manα1-6)Manβ1-4GlcNAcβ1-4GlcNAc. The basic outer branch is Galβ1-4GlcNAc (N-acetyllactosamine), onto which other sugar residues may attach, forming various structures. Kornfeld et al., *Ann. Rev. Biochem.* 54:631 (1985). Sialylation (α2-3 or 6-linked) at the Gal residue is one of the most common substitutions. Based on the general structural scheme, oligosaccharides were sequentially digested with exoglycosidases and the digested products were analyzed in FACE gels.

The results showed that N5-b1 is a 7.3 DP species. Digestion of N5-b1 with NANaseIII caused an upward band shift to 9.2 DP, which indicates the loss of two charged Sia residues. Similar band shifts were observed with N1-b and N5-a, whereas a change of +3 DP units, corresponding to the loss of three Sia residues, was associated with N5-b2 and N5-c. Except for N1-c, none of these oligosaccharides (N1-b and all N5 species) were digested with galactosidases (GALaseIII and GALaseα) without prior NANaseIII treatment, suggesting that their outer branches were all blocked by terminally or internally attached Sia residues. N1-c was not sialylated because no band shift was observed after NANaseIII digestion.

Digestion of desialyated N5-b1 with GALaseIII resulted in a downward band shift of 1.2 DP due to the removal of one Gal residue. Subsequent digestion with HEXaseIII resulted in the removal of only one GlcNAc residue. These results showed that one of the outer four branches of N5-b1 was Siaα2-3(or 6)Galβ1-4GlcNAc. When the desialyated N5-b1 was digested with GALaseIII plus GALaseα, the resulting oligosaccharide migrated to about 6.1 DP. N5-b1 was determined to contain a total of three Gal residues. In separate analyses, digestion with GALaseα alone released just one galactose from the desialyated N5-1, indicating that one of the three galactoses was α1-3 linked to the next sugar residue, and subsequent digestion with HEXaseIII did not release any GlcNAc, suggesting that this Gal was not directly linked to GlcNAc.

The sum of these results indicate that the other outer branch of N5-b1 should be sialylated Galα1-3Galβ1-

4GlcNAc, which is the α-galactosyl epitope. Similar analyses were applied to other carbohydrate species and the sequencing profiles showed that they contained either two (N1-b, N1-c and N5-a) or three (N5-b2 and N5-c) outer branches. The α-galactosyl epitope was found in all major carbohydrate species: N1-b, N5-b1 and N5-b2 contained one sialylated α-galactosyl epitope, N5-c contained two sialylated epitopes, while N1-c had two asialylated epitopes. See FIG. 4.

The presence of the α-galactosyl epitope was also determined by measuring the binding of IB4 to F(ab')$_2$ fragments of hLL2HCN1 and hLL2HCN5. FIG. 6 shows the dose-dependent binding of IB4 to the antibody fragments. Since the only carbohydrates found in these fragments were from the engineered CH1-appended sites, the results support the conclusion that CH1-associated carbohydrates included α-galactosyl epitopes.

Computer modeling studies indicated that the engineered carbohydrate groups are located at highly exposed positions. See FIG. 2. In addition, the results of Tables 1 and 2 indicate that the presence of these CH1-appended carbohydrates on hLL2HCN1 and hLL2HCN5 did not affect their immunoreactivities when compared with that of the parent hLL2. Moreover, these sites are available for conjugation with chelates or drugs without significant effect on the immunoreactivity of the antibodies. This observation indicates that glycosylation at the HCN1 and HCN5 sites in the CH1 domain should not have adverse effects on the overall structure of the Mab, and that the α-galactosyl epitope should be freely accessible for binding with α-Gal antibodies.

TABLE 1

Site-Specific Conjugation of DTPA and Radiolabeling

| F(ab')$_2$ | DTPA | $^{111}$In labeling | | ID$_{50}$ | % of hLL2[c] |
|---|---|---|---|---|---|
| | | % incorp[a] | μCi/μg[b] | | |
| hLL2 | Non-conjug | NA | NA | 0.384 (±0.021) | 100 |
| hLL2HCN1 | Non-conjug | NA | NA | 0.355 (±0.038) | 92.4 |
| | Conjugated | 92 | 6 | 0.387 (±0.042) | 100.8 |
| hLL2HCN5 | Non-conjug | NA | NA | 0.443 (±0.039) | 115.4 |
| | Conjugated | 91 | 5.6 | 0.356 (±0.077) | 92.7 |

[a]Determined by colbalt/cobalt-57 or indium/indium-111 assays. Meares et al., Anal. Biochem. 142:68 (1984).
[b]HPLC yields; percentage of labeling in each case was higher using ITLC analysis; colloidal metal was less than 1% in all labelling.
[c]On the basis of comparisons to the ID$_{50}$ of unmodified control (F(ab')$_2$ in competitive binding assays.

TABLE 2

Site-Specific Conjugation of Doxorubicin

| F(ab')$_2$ | Dextran-Dox | Yield[a] (%) | Efficiency[b] | Immunoreactivity (%) | |
|---|---|---|---|---|---|
| | | | | Cell Binding[c] | ELISA[d] |
| hLL2 | Non-conjug | NA | NA | 100 | 100 |
| | Conjugated | 55 | 5.1 | 41.9 | 42.2 |

TABLE 2-continued

Site-Specific Conjugation of Doxorubicin

| F(ab')$_2$ | Dextran-Dox | Yield[a] (%) | Efficiency[b] | Immunoreactivity (%) | |
|---|---|---|---|---|---|
| | | | | Cell Binding[c] | ELISA[d] |
| hLL2HCN1 | Non-conjug | NA | NA | 100 | 100 |
| | Conjugated | 30 | 6.8 | 70 | 70.6 |
| hLL2HCN5 | Non-conjug | NA | NA | ND | 100 |
| | Conjugated | 80 | 7.2 | ND | 94.8 |

[a]Determined by spectrophotometry.
[b]Values for DOX/F(ab')$_2$ were determined and calculated by spectrophotometry.
[c]Activity determined by a cell surface binding assay as calculated from the ID$_{50}$ values.
[d]Immunoreactivity calculated from ID$_{50}$ values.

EXAMPLE 3

Treatment of *Cryptococcus neoformans* Infections in AIDS Patients

Patients infected with HIV have lost their immune resistance to a variety of opportunistic infections such as *Cryptococcus neoformans*. Treatment with anti-fungal drugs, such as amphotericin B or fluconazole, is usually not every effective. It has been suggested that anti-fungal Mabs, when used in conjunction with conventional anti-fungal drugs, can be an effective modality for the treatment of *C. neoformans* infection in AIDS patients. Since AIDS patients are immunosuppressed, however, the effectiveness of antibody-based therapy, which might also require cellular immunity, has been questioned. Nevertheless, human serum, even under massive immunosuppressive regimens, exhibited significant levels of circulating anti-Gal. Galili et al. *J. Exp. Med.* 160:1519 (1984).

The murine Mab 2H1 is specific for the capsular polysaccharide glucuronoxylomannan (GXM) in *C. neoformans* and has demonstrated therapeutic efficacies against the organisms when used in conjunction with conventional anti-cryptococcal drugs. Mukherjee et al., *Antimicrob. Agents Chemotherap.* 38: 580 (1995). By engineering N-linked glycosylation sites, such as the HCN1 or HCN5 sites, into the CH1 domain of 2H1, or the VK-appended site found in mLL2, into the corresponding VK regions of other monoclonal antibodies, an α-galactosyl epitope would be expected to be expressed. Regardless of the compromised immune response of the patients, the α-galactosyl epitope in the antibody will interact with the circulating anti-Gal, eliciting a complement response that will kill the organisms directly. In addition, the opsonized organisms will be phagocytosed by antigen presenting cells and assist the development of a cellular and/or humoral immune response against the organism.

Similarly, antibodies specific to different infectious organisms (e.g., tuberculosis, pneumocystis carinii, or viruses) can be engineered with the α-galactosyl epitope and used for the elimination of the different organisms through the actions of complement activation and/or development of cellular/humoral immunity mediated by anti-Gal. Anti-Gal mediated viral inactivation via complement activation is believed to play a role in the prevention of the transmission of type C retrovirus to humans. Rother et al., *J. Exp. Med.* 182:1345 (1995). This should be applicable to both healthy or immunosuppressed patients infected with the organisms.

EXAMPLE 4
α-Gal Antibody-induced Specific Tumor Killing

As discussed above, there is a sizable collection of Mabs that are specific for a variety of TAAS. One of the mostly widely studied TAA has been the human carcinoembryonic antigen (CEA). The murine Mab, MN-14, a class III CEA-specific antibody with demonstrated clinical efficacies for the detection and treatment of various CEA-expressing cancers, is cited here as an example. This Mab has been humanized (hMN-14), and the hMN-14 exhibits in vivo targeting in patients. Shevitz et al., *Proc. J. Nucl. Med.* 34:217p (1993); Sharkey et al., *Cancer Res.* 55: 5935s (1995). The HCN1 and/or HCN5 sites can be engineered into the CH1 domain of hMN-14, and expressed in the murine myeloma, SP2/0 cells. The α-Gal-hMN-14 antibody can be injected into cancer patients either as whole IgG, F(ab')$_2$, Fab' or Fab. Procedures to prevent early neutralization of the injected antibodies are discussed above.

After the α-Gal-hMN-14 has targeted the tumor sites, and the level of anti-Gal restored to normal, complex formation of anti-Gal on the tumor cell surface bound with α-Gal-hMN-14 will elicit CDCC and those opsonized cells will be phagocytosed by antigen presenting cells. The specific TAA (s) associated with the tumor will be properly presented to develop tumor-specific immunity. This approach should be applicable to any antibody, preferably a slowly internalizing antibody having tumor specificity.

EXAMPLE 5
Treatment of HIV-infected Patients

HIV positive patients exhibit a latent period of retroviral infection before a full-blown disease is manifested. A variety of anti-HIV antibodies specific for markers such as surface proteins, structural proteins, or enzymes have been developed. Other T cell specific antigens, such as CD4 and fusin, can also be chosen as a target of attack. These antibodies specific for HIV markers can be engineered with α-galactosyl epitopes and used to target HIV+ cells using procedures described above. HIV+ cells are killed by anti-Gal mediated complement activation, and by the development of anti-HIV immunity as HIV+ cells opsonization will assist the antigen presenting cells to digest and sort out appropriate HIV-specific antigens for immune enhancement. This kind of treatment is most appropriate for healthy individuals who have been tested HIV+.

EXAMPLE 6
Development of Anti-anti-id Responses as a Tumor Vaccine

The anti-id antibody, WI2, against the idiotype of MN-14, has been shown to be an Ab2β. Losman et al., *Int. J. Cancer* 56:580 (1994). Sera from NZW rabbits immunized with WI2 were immunoreactive to CEA, indicating that WI2 served effectively as a surrogate antigen for CEA and can potentially be used as a tumor vaccine. This rat WI2 anti-id antibody against MN-14 was humanized (hWI2), and it has been used as a clearing agent for pretargeting. Leung et al., *Proc. Amer. Assoc. Cancer Res.* 37: 468 (1996).

α-Galactosyl epitopes can be engineered into hWI2 (α-Gal-hWI2) and the α-Gal-hWI2 can then be used as an effective tumor vaccine because the presence of the α-galactosyl epitope will enhance antigen presenting cell processing mediated by anti-Gal and stimulate a strong Ab3, or anti-CEA response. Similar approaches can be taken to raise antibodies against weakly immunogenic proteins, glycoproteins, peptides, glycopeptides, carbohydrates or other small molecules.

EXAMPLE 7
Use of α-Gal Antibody as a Clearing Agent for Pre-targeting

Anti-id antibodies can be used as a clearing agent for pretargeting. For example, the humanized hWI2 anti-id antibody to the anti-CEA hMN-14 has been used as the clearing agent for the removal of unbound and circulating hMN-14 in a pretargeting protocol. Galactose has been conjugated to hWI2 to speed up blood clearance after hWI2 complex formation with circulating hMN-14. However, problems such as liver accumulation of complexed hMN-14 have rendered the use of Gal-conjugation undesirable. Instead, hWI2 can be engineered with the α-galactosyl epitope. The patient can be injected with the targeting hMN-14 (conjugated either with streptavidin or biotin). Anti-Gal is removed from circulation by administration of synthetic free α-galactosyl epitope or related oligosaccharides prior to the injection of the α-Gal-hWI2 clearing agent. Rapid clearance of the hMN-14 complexed with α-Gal-hWI2 occurs when the level of anti-Gal returns to normal. Secondary radiolabeled effector molecules, such as DTPA-biotin or DTPA-streptavidin, can be administered to achieve tumor-specific radiation.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A method for stimulating humoral and cellular immune responses in a catarrhine primate against a tumor that expresses a tumor associated antigen (TAA) or against a disease caused by an infectious agent, said method comprising the step of:
   (a) administering an alpha-Gal antibody to the mammal, wherein said alpha-Gal antibody comprises:
      (i) an antibody component that binds with a specified target epitope, wherein said target epitope is an epitope of a TAA or an epitope of an antigen associated with an infectious agent, and
      (ii) at least one alpha-galactosyl epitope, wherein said alpha-Gal antibody can form a complex with cells that express said target epitope and antibodies that bind said alpha-galactosyl epitope and wherein complex formation is prevented initially following administration of alpha-Gal antibody either by pre-treating to clear endogenous antibodies that bind alpha-Gal epitope or by shielding alpha-Gal epitope from recognition by endogenous antibodies that bind alpha-Gal epitope.

2. The method of claim 1, wherein said antibody component is selected from the group consisting of:
   (a) a murine monoclonal antibody;
   (b) a humanized antibody derived from a murine monoclonal antibody;
   (c) a human monoclonal antibody; and
   (d) an antibody fragment derived from (a), (b) or (c).

3. The method of claim 2, wherein said antibody fragment is selected from the group consisting of $F(ab')_2$, $F(ab)_2$, Fab' and Fab.

4. The method of claim 1, wherein said antibody component comprises at least one α-galactosyl epitope that is sialylated.

5. The method of claim 1, wherein said method further comprises the step of administering an oligosaccharide prior to or during step (a), wherein said oligosaccharide specifically binds with antibodies that bind the α-galactosyl epitope.

6. The method of claim 1, wherein said method further comprises the step of administering an oligosaccharide prior to step (a), wherein said oligosaccharide specifically binds with antibodies that bind the alpha-galactosyl epitope.

* * * * *

SEQUENCE LISTING

<160> NUMBER OF SEQ ID NOS: 4

<210> SEQ ID NO 1
<211> LENGTH: 49
<212> TYPE: PRT
<213> ORGANISM: Homo sapiens

<400> SEQUENCE: 1

Pro Glu Pro Val Thr Val Ser Trp Asn Ser Gly Ala Leu Thr Ser Gly

-continued

```
                1               5              10              15
Val His Thr Phe Pro Ala Val Leu Gln Ser Ser Gly Leu Tyr Ser Leu
               20              25              30
Ser Ser Val Val Thr Val Pro Ser Ser Ser Leu Gly Thr Gln Thr Tyr
       35              40              45
Ile
```

<210> SEQ ID NO 2
<211> LENGTH: 49
<212> TYPE: PRT
<213> ORGANISM: Homo sapiens

<400> SEQUENCE: 2

```
Pro Glu Pro Val Thr Val Ser Trp Asn Ser Ala Leu Thr Ser Gly
  1               5              10              15
Val His Thr Phe Pro Ala Val Leu Gln Ser Ser Gly Leu Tyr Ser Leu
               20              25              30
Ser Ser Val Val Thr Val Pro Ser Ser Ser Leu Gly Thr Gln Thr Tyr
       35              40              45
Ile
```

<210> SEQ ID NO 3
<211> LENGTH: 49
<212> TYPE: PRT
<213> ORGANISM: Homo sapiens

<400> SEQUENCE: 3

```
Pro Glu Pro Val Thr Val Ser Trp Asn Ser Gly Ala Leu Thr Ser Gly
  1               5              10              15
Val His Thr Phe Pro Ala Val Leu Gln Ser Ser Gly Leu Tyr Ser Leu
               20              25              30
Ser Ser Val Val Thr Val Pro Ser Ser Ser Asn Gly Thr Gln Thr Tyr
       35              40              45
Ile
```

<210> SEQ ID NO 4
<211> LENGTH: 4
<212> TYPE: PRT
<213> ORGANISM: Homo sapiens

<400> SEQUENCE: 4

Ser Arg Ile Phe